(12) United States Patent
Kasai

(10) Patent No.: US 7,183,508 B2
(45) Date of Patent: Feb. 27, 2007

(54) CONNECTOR

(75) Inventor: Tokuo Kasai, Kyoto (JP)

(73) Assignee: Arkray Inc., Kyoto (JP)

( * ) Notice: Subject to any disclaimer, the term of this patent is extended or adjusted under 35 U.S.C. 154(b) by 0 days.

(21) Appl. No.: 11/304,576

(22) Filed: Dec. 16, 2005

(65) Prior Publication Data

US 2006/0121759 A1 Jun. 8, 2006

Related U.S. Application Data

(63) Continuation of application No. PCT/JP04/08360, filed on Jun. 15, 2004.

(30) Foreign Application Priority Data

Jun. 16, 2003 (JP) ............................. 2003-170615
Sep. 12, 2003 (JP) ............................. 2003-321984

(51) Int. Cl.
*H01R 33/96* (2006.01)
(52) U.S. Cl. .................................... 200/51.09; 439/188
(58) Field of Classification Search ... 200/51 R–51.13; 439/62, 188, 630
See application file for complete search history.

(56) References Cited

U.S. PATENT DOCUMENTS

| | | | |
|---|---|---|---|
| 5,924,881 A * | 7/1999 | Yasushi et al. | 439/188 |
| 5,949,160 A * | 9/1999 | Anderson et al. | 307/140 |
| 6,435,887 B2 * | 8/2002 | Koitsalu | 439/188 |
| 6,576,853 B2 * | 6/2003 | Motojima | 200/51.09 |
| 6,692,276 B1 * | 2/2004 | Abe et al. | 439/188 |
| 6,899,557 B2 * | 5/2005 | Hirata | 439/188 |
| 6,994,576 B2 * | 2/2006 | Tanaka et al. | 439/188 |

FOREIGN PATENT DOCUMENTS

| | | |
|---|---|---|
| JP | 5-21217 Y2 | 5/1989 |
| JP | 8-10208 B2 | 7/1991 |
| JP | 10-332626 A | 12/1998 |
| JP | 11-40270 A | 2/1999 |
| JP | 2002-343505 A | 11/2002 |
| JP | 2002324629 A * | 11/2002 |
| JP | 2003-059595 A | 2/2003 |

OTHER PUBLICATIONS

International Search Report for PCT/JP2004/008360, mailed Aug. 31, 2004, 4 pgs.

* cited by examiner

*Primary Examiner*—Michael A. Friedhofer
(74) *Attorney, Agent, or Firm*—Sterne, Kessler, Goldstein & Fox, P.L.L.C.

(57) ABSTRACT

In a connector, the position at which a pointed part of a rocking terminal slidingly contacts an insertion and the position at which the pointed part of the rocking terminal contacts an upper surface of a terminal plate are substantially the same. Therefore, shavings generated by the contact of the insertion and the pointed part or foreign matters adhering to the insertion may adhere to the pointed part of the rocking terminal and be pinched between the pointed part and the terminal plate, whereby no contact is caused by inserting the insertion into the connector. Then, with regard to a connector having a switch part comprising a rocking terminal (51) swayed by inserting an insertion (53) into a main body of the connector and a receiving terminal (52) arranged to contact the rocking terminal, a pointed part (51a) is formed on the rocking terminal, and the terminals contact electrically with each other by making the receiving terminal touch a side surface of the pointed part.

6 Claims, 14 Drawing Sheets

CONNECTOR

TECHNICAL FIELD

The present invention relates to a connector having a switch construction that terminals contacting with each other are provided in the connector, and the terminals are turned into contact or no contact by inserting an insertion into the connector.

Concretely, the present invention relates to an art of a connector, which has a switch part constructed by providing a plurality of terminals contacting with each other in the connector so as to identify insertions inserted into the connector by the switch part turned on or off by inserting an insertion, for preventing contact failure and the like caused by foreign matters at the contact part.

BACKGROUND ART

Conventionally, a switch construction may be provided in a connector connecting electronic members or electric apparatus. With regard to the switch construction, two switch terminals are short-circuited (contacted) with each other and provided in the mold of the connector. By inserting an insertion into the mold of the connector of an electronic member or electric apparatus, the contact part of the terminals, that is, the short-circuit part is separated (released) or contacted.

As conventional examples of the above-mentioned switch construction, working principle thereof, and use thereof, there are following conventional arts.

As examples of a connector of measuring apparatus, there are arts described in the Japanese Patent Hei. 08-10208, the Japanese Patent Laid Open Gazette Hei. 10-332626.

Next, explanation will be given on the contact part of terminals of connector of the conventional art according to FIGS. 10, 11, 12 and 13. FIG. 10 is a perspective view of the conventional connector 3 and an insertion 2 inserted into the connector 3. FIG. 11 is a drawing of the pile of the conventional insertion 2, rocking terminals 1 and 11, and terminal plate 4 which the rocking terminal 1 contacts. FIG. 12 is a cross-sectional side view of the positional relation among the conventional connector 3, the rocking terminal 1 and a terminal engaging opening 2a opened in the insertion 2. FIG. 13 is a drawing of the insertion 2 inserted into the connector 3 in the conventional construction.

A connector insertion hole 3a, which the insertion 2 is inserted into, is provided in the connector 3. Rocking terminals 1 and 11 are projected in parallel inside the connector insertion hole 3a. Pointed parts 1a and 11a are extensionally provided downward on the tip of the rocking terminals 1 and 11, and the terminal plate 4 is arranged below the rocking terminals 1 and 11. Normally, the lower end of the pointed parts 1a and 11a and the upper surface of the terminal plate 4 connect electrically with each other. The terminal engaging opening 2a is provided in the insertion 2 so that the kind of the insertion 2 or apparatus connected to the insertion 2 is identified.

With regard to the conventional art, the pointed parts 1a and 11a of the rocking terminals 1 and 11 connect the upper surface of the terminal plate 4, and by inserting the insertion 2 through the connector insertion hole 3a, the tips of the rocking terminals 1 and 11 are raised as shown in FIG. 13. Accordingly, the contact of the tips of the rocking terminals 1 and 11 and the terminal plate 4 is canceled once. Then, by inserting the insertion 2 through the connector insertion hole 3a further, the pointed parts 1a and 11a of the rocking terminals 1 and 11 engage with the terminal engaging opening 2a of the insertion 2 and move downward, whereby the pointed parts 1a and 11a contacts the terminal plate 4 again.

Patent Literature 1: the Japanese Patent Hei. 8-10208

Patent Literature 2: the Japanese Patent Laid Open Gazette Hei. 10-332626

However, with regard to such the conventional art, the position at which the pointed part 1a (11a) of the rocking terminal 1 (11) slidingly contacts the insertion 2 and the position at which the pointed part 1a of the rocking terminal 1 contacts the upper surface of the terminal plate 4 are substantially the same in the connector 3. Therefore, shavings generated by the contact of the insertion 2 and the pointed part 1a or foreign matters adhering to the insertion 2 may adhere to the pointed part 1a of the rocking terminal 1 and be pinched between the pointed part 1a and the terminal plate 4, whereby no contact is caused by inserting the insertion 2 into the connector 3.

Furthermore, by inserting the insertion 2, high voltage static electricity generated at the outside may flow into the rocking terminal 1 (11) through the insertion 2, whereby the high voltage may damage electric apparatus connected to the connector 3.

Such problems of the conventional art will be solved by the present invention.

DISCLOSURE OF INVENTION

Problems to be Solved by the Invention

The problems to be solved by the present invention is that shavings generated by the contact of a pointed part of a rocking terminal and an insertion or foreign matters adhering to the insertion may adhere to the pointed part of the rocking terminal in a connector so as to cause no contact.

Means for Solving the Problems

According to the present invention, with regard to a connector having a switch part comprising a rocking terminal swayed by inserting an insertion into a main body of the connector and a receiving terminal arranged to contact the rocking terminal, an pointed part is formed on the rocking terminal, and the terminals contact electrically with each other by making the receiving terminal touch a side surface of the pointed part.

With regard to the connector of the present invention, the receiving terminal is provided at a position opposite to the rocking terminal, the pointed part of the rocking terminal is constructed acutely, an engaging part is provided on the receiving terminal at a position opposite to the pointed part, and the terminals contact electrically with each other by making the engaging part and the pointed part engage with each other.

According to the present invention, with regard to a connector having a switch part comprising a rocking terminal swayed by inserting an insertion into a main body of the connector and a receiving terminal arranged to contact the rocking terminal, a part of the rocking terminal slidingly contacting the insertion inserted into the connector and a part of the rocking terminal electrically contacting the receiving terminal are constructed separately.

With regard to the connector of the present invention, a pointed part is formed on the rocking terminal, and an electrical contact part of the rocking terminal and the receiving terminal is constructed to be separated from the pointed part.

With regard to the connector of the present invention, a pointed part is formed on the rocking terminal, and an electrical contact part contacting the receiving terminal is constructed on the rocking terminal at a position near and above or below the pointed part.

With regard to the connector of the present invention, the part of the rocking terminal slidingly contacting the insertion is constructed by a nonconductor.

Effect of Invention

The present invention constructed as the above brings the following effects. According to the present invention, with regard to a connector having a switch part comprising a rocking terminal swayed by inserting an insertion into a main body of the connector and a receiving terminal arranged to contact the rocking terminal, a pointed part is formed on the rocking terminal, and the terminals contact electrically with each other by making the receiving terminal touch a side surface of the pointed part. Accordingly, foreign matters are never accumulated on the side surface of the pointed part so as to keep the contact part clean always, whereby contact failure is prevented so as to ensure the electrical contact.

With regard to the connector of the present invention, the receiving terminal is provided at a position opposite to the rocking terminal, the pointed part of the rocking terminal is constructed acutely, an engaging part is provided on the receiving terminal at a position opposite to the pointed part, and the terminals contact electrically with each other by making the engaging part and the pointed part engage with each other. Accordingly, even if foreign matters adhere to the pointed part, the foreign matters fall down through the engaging opening by inserting the pointed part into an engaging hole as the engaging opening, it cause the electrical contact to be ensured.

According to the present invention, with regard to a connector having a switch part comprising a rocking terminal swayed by inserting an insertion into a main body of the connector and a receiving terminal arranged to contact the rocking terminal, a part of the rocking terminal slidingly contacting the insertion inserted into the connector and a part of the rocking terminal electrically contacting the receiving terminal are constructed separately. Accordingly, foreign matters generated in the part slidingly contacting the insertion is prevented from adhering to or accumulated on the electrically contacting part, whereby the rocking terminal and the receiving terminal contact electrically stably so as to improve the quality of the switch part.

With regard to the connector of the present invention, a pointed part is formed on the rocking terminal, and an electrical contact part of the rocking terminal and the receiving terminal is constructed to be separated from the pointed part. Accordingly, the insertion is separated from the contact part so that the insertion does not interfere with the electrical contacting operation, whereby the electrical contact is ensured.

With regard to the connector of the present invention, a pointed part is formed on the rocking terminal, and an electrical contact part contacting the receiving terminal is constructed on the rocking terminal at a position near and above or below the pointed part. Accordingly, the vertical movement of the pointed part by inserting the insertion is directly transmitted as the width of the vertical movement of the electrical contact part, whereby the width of movement of the electrical contact part can be extended so as to improve ON-OFF accuracy of the switch.

With regard to the connector of the present invention, the part of the rocking terminal slidingly contacting the insertion is constructed by a nonconductor. Accordingly, high voltage is not applied on an electrical apparatus connected to the rocking terminal or the receiving terminal so as to prevent the apparatus to be damaged by static electricity.

Figure 1:
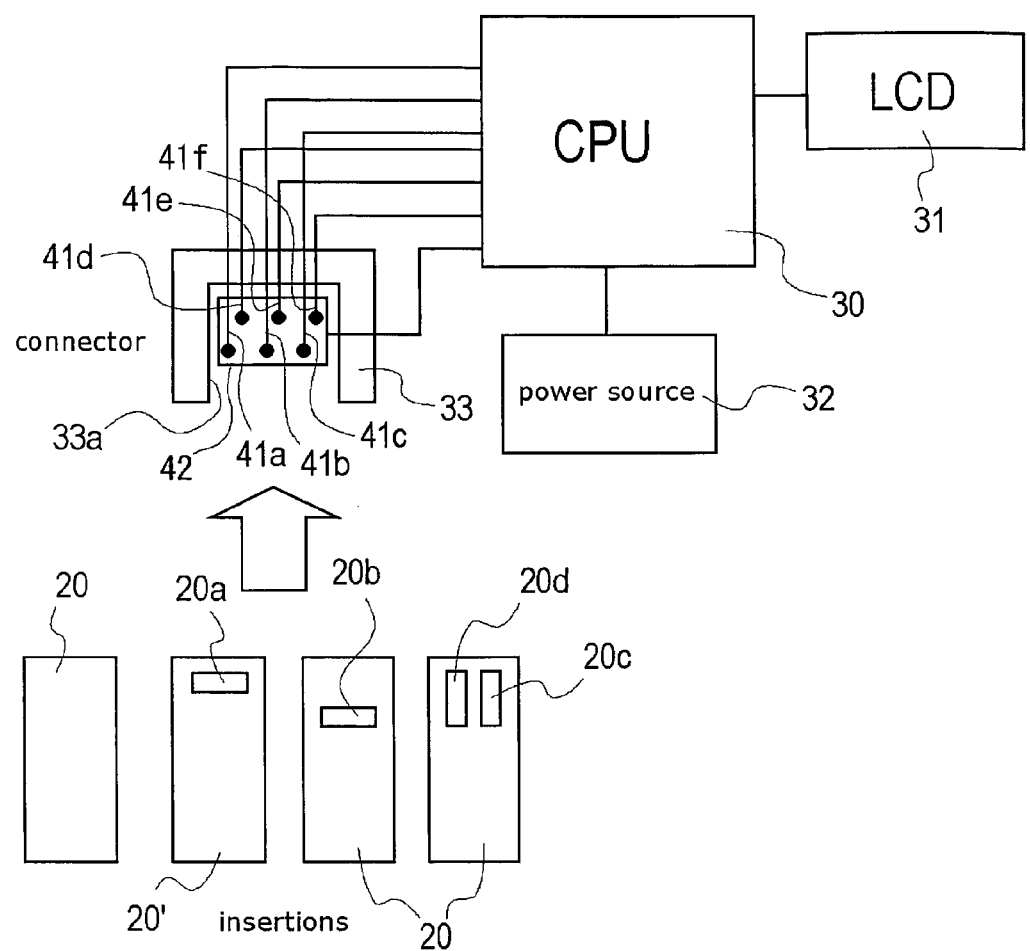
FIG. 1 is a block diagram of an embodiment in which switch construction of the present invention is adopted.

DESCRIPTION OF NOTATIONS 20, 21, 23 and 53 insertions
33 and 34 connectors
51, 54, 57 and 60 rocking terminals
51a, 54a and 60a pointed parts
52, 55, 56 and 61 receiving terminals
56a an engaging part

BEST MODE FOR CARRYING OUT THE INVENTION

Next, explanation will be given on an embodiment of the present invention.

Figure 2:
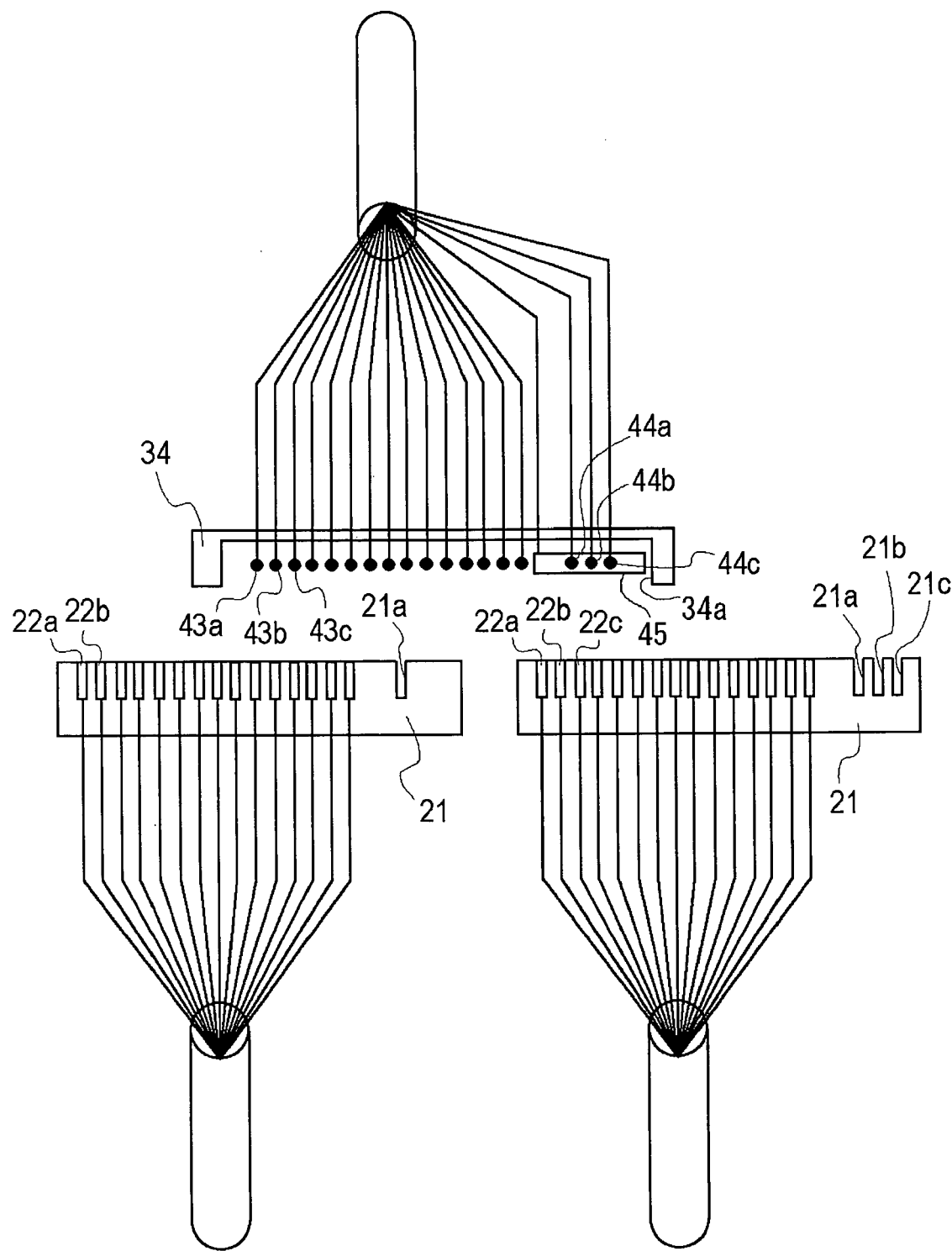
FIG. 2 is a drawing of another embodiment in which the switch construction of the present invention is adopted.

FIG. 1 is a block diagram of an embodiment in which switch construction of the present invention is adopted, and FIG. 2 is a drawing of another embodiment in which the switch construction of the present invention is adopted.

In the embodiment shown in FIG. 1, a connector having the switch construction of the present invention is adopted in a toy. A central processing unit (CPU or control unit) 30 is connected to a display unit (LCD) 31, a power source 32, a receiving terminal 42 comprising a plate, and each rocking terminals 41a, 41b and the like in a connector 33.

The rocking terminals 41a, 41b and the like and the receiving terminal 42 are stored in a main body of the connector 33 and contact with each other. A connector insertion hole 33a is opened in the main body of the connector 33 so that an insertion 20 constructed by a chip can be inserted into the connector insertion hole 33a. Some kinds of the insertions 20 are provided, and engaging openings 20a, 20b and the like of different shape, direction or number are opened in the insertions 20 for each of the kinds of the insertions 20.

In this construction, by inserting one insertion 20 into the connector insertion hole 33a of the connector 33, any of the rocking terminals 41a, 41b and the like contacts the receiving terminal 42.

Namely, the switch part is constructed so that any of the rocking terminals 41a, 41b and the like electrically contacting the receiving terminal 42 is changed according to the kind of the insertion 20. The central processing unit 30 recognizes the rocking terminal contact or no contact, whereby a program corresponding to the kind of the insertion 20 is executed.

In this embodiment, a data, such as a picture or a game, is read and displayed on the display unit 31.

The data is memorized by a ROM or RAM (not shown) and an address is assigned to the data so that a combination of one of the rocking terminals 41a, 41b and the like and the receiving terminal 42 corresponds to the address. Concretely, in the case of the insertion 20' in FIG. 1, the rocking terminals 41d, 41e and 41f contact the receiving terminal 42 so that a picture or a game corresponding to this combination is displayed on the display unit (LCD) 31.

In the embodiment in FIG. 2, a connector having the switch construction of the present invention is used for distinguish printer cables (manufacturers thereof) from each other. Namely, a connector insertion hole 34a is opened in a main body of a connector 34 so that an insertion (connector) 21 can be inserted into the connector insertion hole 34a. The connector 34 is provided therein with terminals 43a, 43b and the like, and rocking terminals 44a, 44b and 44c and a receiving terminal 45 constituting a switch part, and each of them is connected to the control unit such as a computer. On the other hand, the insertion 21 connected to the connector 34 is provided therein with terminals 22a, 22b and the like for the control and the data, and openings 21a, 21b and the like, each of them assigned to the different manufacturer respectively. The terminals 22a, 22b and the like are connected to the control unit of the main body of the printer.

In this construction, only by inserting the insertion 21 into the connector 34, either of the rocking terminals 44a, 44b and 44c contact the receiving terminal 45 at the switch part, whereby the control unit selects a manufacturer corresponding to this combination and reads the data of the manufacturer so as to set a driver automatically.

Figure 3:
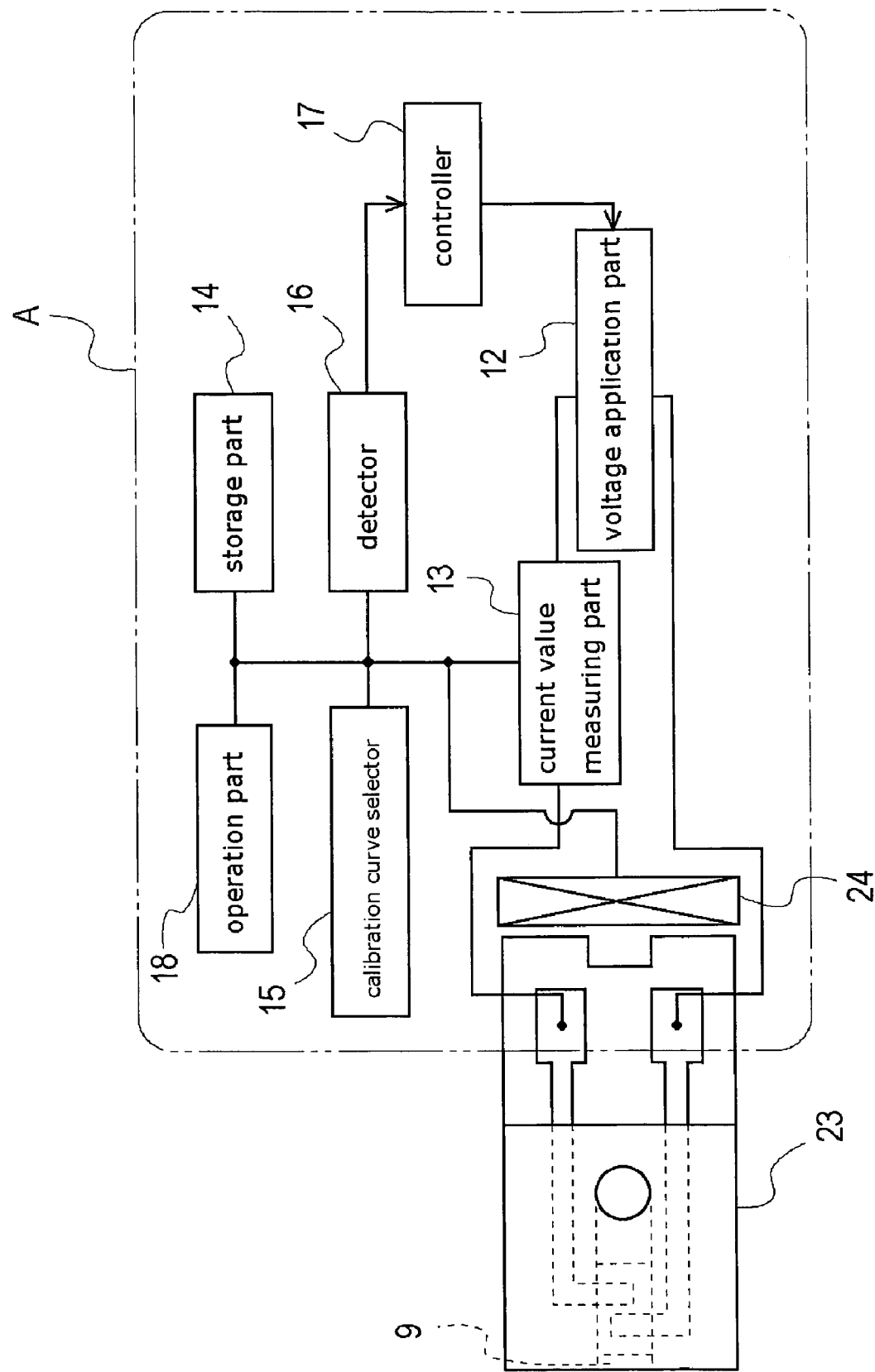
FIG. 3 is a drawing of a simple blood glucose level measuring device in which the switch construction of the present invention is adopted.
Figure 4:
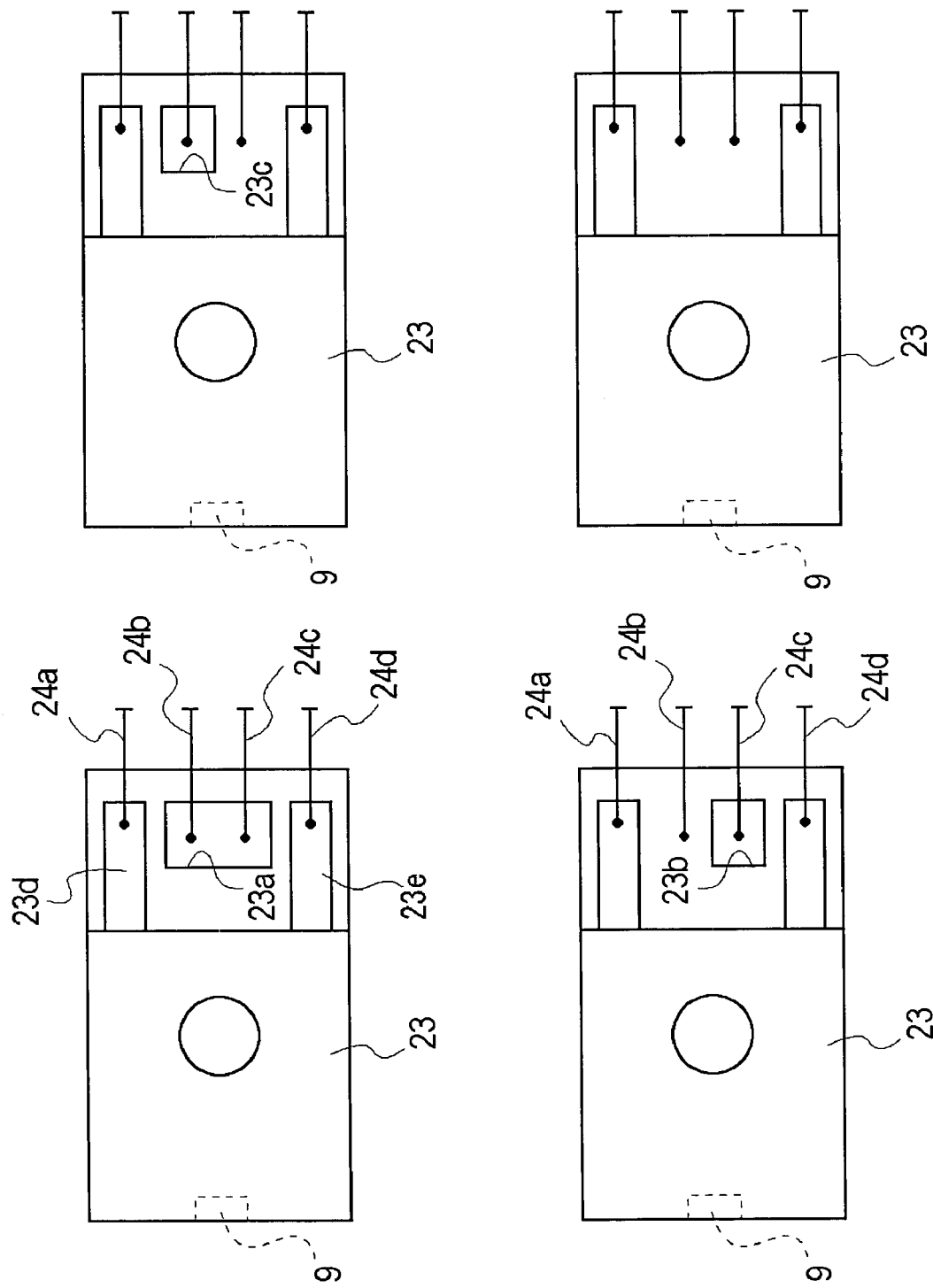
FIG. 4 is a drawing of a biosensor 23 as an insertion inserted into the simple blood glucose level measuring device in FIG. 3.

FIG. 3 is a drawing of the third embodiment that a connector having the switch construction of the present invention is used in a simple blood glucose level measuring device, and FIG. 4 is a drawing of a biosensor 23 as an insertion inserted into the simple blood glucose level measuring device in FIG. 3. The simple blood glucose level measuring device is always carried by a diabetic so as to check the blood glucose level simply for judging whether dosage of insulin is required or not, and whether the diabetic is in low blood glucose or not.

For measuring the concentration of a specified component in body fluid, such as glucose in blood, there is a general method that uses oxidation-reduction reaction with redox enzyme as a catalyzer. On the other hand, for measuring the blood glucose level simply at home or the place where a diabetic has gone, a hand-held simple blood glucose level measuring device is commonly used. Oxidation reaction is performed in the simple blood glucose level measuring device, and a disposable biosensor is attached to the device and then blood is supplied to the biosensor so as to measure the blood glucose level.

The sensitivity of each of biosensors is not always the same, and fluctuates caused by the change of materials or design of manufacturing line.

Especially, at the early stage of starting the manufacturing line, it is necessary to optimize conditions and select materials, whereby the sensitivity of the sensors tends to fluctuate.

In the case that biosensors are manufactured at a plurality of factories or on a plurality of manufacturing lines in one factory, the sensitivity of the sensors may fluctuate among the factories or the manufacturing lines.

On the other hand, there is a simple blood glucose level measuring device provided therein with a plurality of calibration curves in consideration of the difference of the sensitivity of the sensors. In addition to this, it is necessary for a measuring device constructed to measure a plurality of items, such as blood glucose level and cholesterol level, to be provided therein with a plurality of calibration curves for each of the measured items.

In such a case, the measuring device must recognize information of a calibration curve suitable to each biosensor or measured item in any way.

The inside of the simple blood glucose level measuring device A is constructed so that the biosensor 23 as the insertion can be inserted thereinto. Blood is dropt from a finger of a diabetic to the biosensor 23, and blood glucose level is calculated from the blood.

Namely, the biosensor 23 as the insertion is constructed so that an electrode system made by carbon is formed on an insulated board by screen printing or another method so as to form a insulating layer, and then the electrode system is covered by a porous material carrying redox enzyme and electron acceptor, and after that, the all members are unified by a holding frame and a cover.

When sample solution is dropt into a sample supply hole 9 on the porous material, the redox enzyme and electron acceptor held by the porous material dissolve in the sample solution and perform enzyme reaction with a substrate in the sample solution, whereby the electron acceptor is deoxidized. After finishing the reaction, the deoxidized electron acceptor is oxidized electrochemically so as to obtain the substrate level in the sample solution based on oxidation current value.

The simple blood glucose level measuring device is provided therein with a current value measuring part 13 measuring the oxidation current value, a voltage application part 12, an operation part 18, a storage part 14, a calibration curve selector 15 selectively detecting the difference between calibration curves of each lot of the biosensor 23 as the insertion, a detector 16 for the calibration curves, and a controller 17 controlling the amount of impressed voltage.

In the present invention, a terminal 24 having the switch construction of the present invention is provided in the calibration curve selector 15.

The terminal 24 is constructed so that engaging openings 23a, 23b and 23c are formed in the tip of the biosensor 23 as the insertion so that the calibration curve corresponding to the lot of the biosensor 23 is selected by whether rocking terminals 24b and 24c contact a receiving terminal through the engaging openings 23a, 23b and 23c or not. In addition, terminals 23d, 23e, 24a and 24d are connected to the power source.

The switch part is provided in the connector and comprises one or more rocking terminals and the receiving terminal, and the insertion having the engaging openings is inserted through the connecter insertion hole so that each rocking terminal and receiving terminal contacts and communicate with each other through the engaging opening or don't contact with each other at a position without the openings, whereby the insertion is identified based on the combination of contact and no contact. In this construction, as the above mentioned, the switch part is constructed so as to prevent the rocking contact part from being no contact by shavings generated in the contact part or foreign matters.

Explanation will be given on the first embodiment of the construction of the switch part in the connector of the present invention according to FIG. 5.

The switch part comprises a rocking terminal 51 swayed vertically by inserting an insertion 53 and a receiving terminal 52 contacting the rocking terminal 51 normally, and the terminals are projected upper and lower parallel with each other from the main body of the connector. The rocking terminal 51 is constructed by electrically-conductive and elastic material, such as spring steel, and the basal end of the rocking terminal 51 is fixed to the main body of the connector and connected to the controller (or electrical apparatus) through wiring. An pointed part 51a is formed at the tip of the rocking terminal 51, and an inclined part 51b for guiding the insertion and an inclined part 51c for guiding the drawing are formed on the side of the pointed part 51a. In this embodiment, the inclined parts are formed by bending the tip of the rocking terminal 51 to be V-shaped in cross-section. The size of the pointed part 51a is constructed so that the pointed part 51a can pass through an engaging opening 53a opened in the insertion 53. In other words, the size of the engaging opening 53a is constructed so that the lower portion of the pointed part 51a can pass through the engaging opening 53a. In addition, the inclined parts 51b and 51c may be constructed by curved surfaces.

The receiving terminal 52 is arranged below the rocking terminal 51 and constructed by electrically-conductive material, such as spring steel. The basal end of the receiving terminal 52 is fixed to the main body of the connector and connected to the controller (or electrical apparatus). The tip of the receiving terminal 52 is bent downward so as to form a contact part 52a L-like shaped in cross-section. The inclined angle of the contact part 52a is substantially the same as that of the inclined part 51c. Furthermore, a salient 52b is formed on the contact part 52a so that the contact part 52a can contact the inclined part 51c even if the angle is changed. Although the salient 52b is semicircular in cross-section, the shape of the salient 52b is not limited thereto, it may alternatively be triangular or the like. Furthermore, the salient 52b may be omitted.

Then, the rear side surface of the pointed part 51a of the rocking terminal 51 normally contacts the salient 52b (or the contact part 52a) of the receiving terminal 52, whereby an electrical contact part is constructed. Namely, the electrical contact part of the rocking terminal 51 and the receiving terminal 52 is formed at the inclined part (side surface) of the pointed part 51a without the lower end thereof. In addition, it may alternatively be constructed so that the inclined part 51b for guiding the insertion contacts the salient 52b.

Accordingly, by inserting the insertion 53 into the insertion hole of the connecter, the tip of the insertion 53 touches the inclined part 51b of the rocking terminal 51 and is inserted while pushing the pointed part 51a upward. By inserting the insertion 53 further, the lower end of the pointed part 51a slides on the insertion 53 and reaches and enters the engaging opening 53a, and then moves downward so that the inclined part 51c for guiding the drawing contacts the salient 52b of the receiving terminal 52. Namely, the rocking terminal 51 contacts the receiving terminal 52, whereby the switch part is turned on.

At this time, the electrical contact part of the pointed part 51a of the rocking terminal 51 and the salient 52b is at the inclined side surface so that, even if shavings or foreign matters on the insertion 53 adhere to the lower end of the pointed part 51a by the slide of the pointed part 51a on the insertion 53, the shavings or foreign matters fall down through the engaging opening 53a.

Accordingly, the electrical contact part is kept clean, thereby preventing contact failure between the rocking terminal 51 and the receiving terminal 52.

Furthermore, the contact position is on the inclined side surface so that, even if foreign matters accumulate thereon, the foreign matters slip and fall down by the shock at the time of taking in and out of the insertion 53, whereby the connection surfaces are kept clean.

In addition, if the engaging opening 53a is not opened at the position of the pointed part 51a of the rocking terminal 51 at the time of inserting the insertion 53, the pointed part 51a keeps on being raised on the upper surface of the insertion 53 and is held so as not to contact the receiving terminal 52, thereby preventing the electrical contact. Namely, the switch part is turned off.

Figure 6:
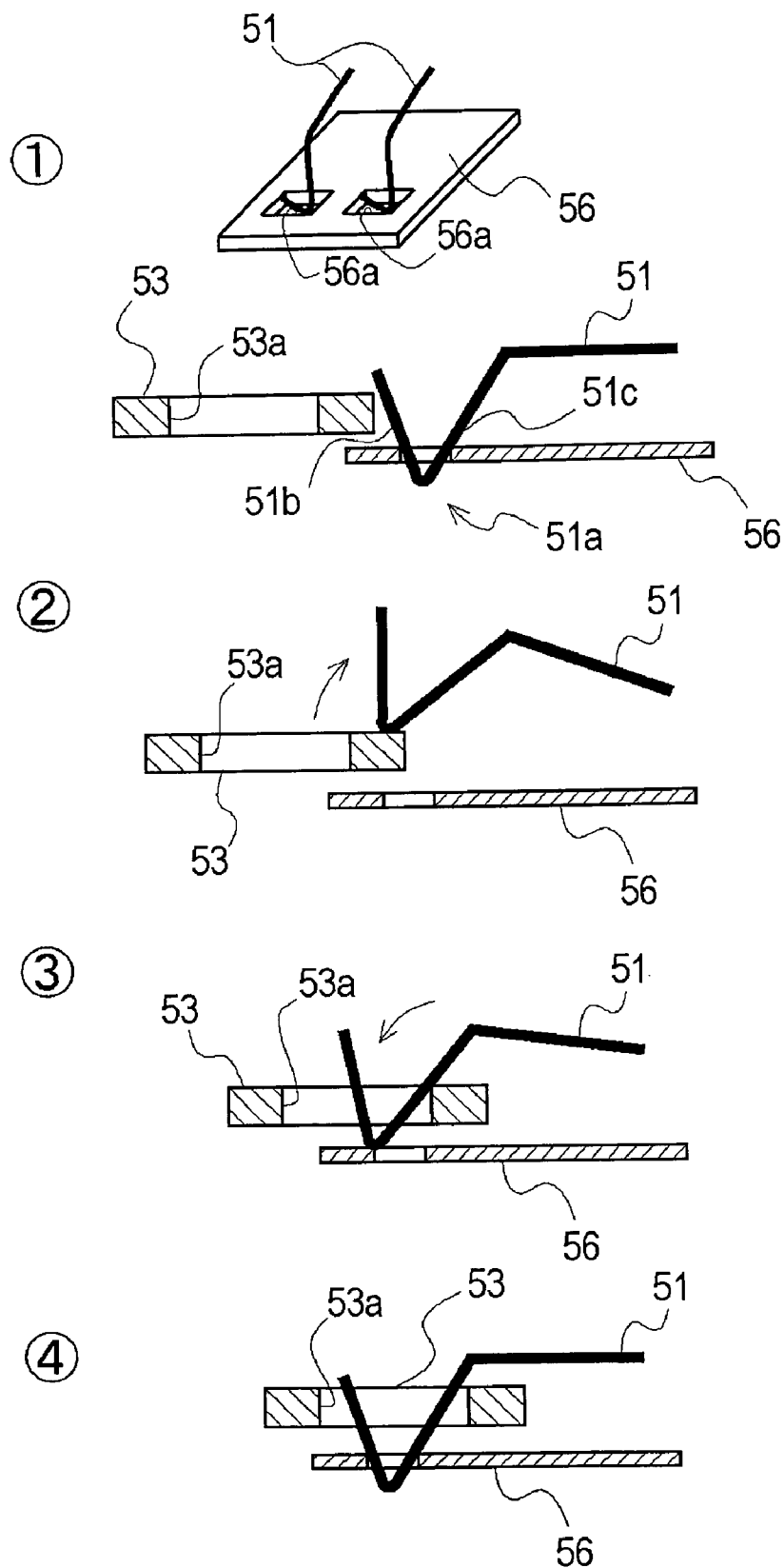
FIG. 6 is a drawing of another embodiment of the switch construction of the present invention.

Next, explanation will be given on the second embodiment of the construction of the switch of the present invention according to FIG. 6.

The switch part comprises the rocking terminal 51 and a receiving terminal 56, and the rocking terminal 51 is constructed the same as that of the first embodiment. The receiving terminal 56 is constructed by an electrically-conductive plate, such as steel plate, and is disposed below the rocking terminal 51 oppositely. The basal end of the receiving terminal 56 is connected to the controller (or electrical apparatus), and an engaging hole 56a is opened at the position corresponding to the pointed part 51a of the rocking terminal 51. Normally, the lower portion of the pointed part 51a is inserted partially into the engaging hole 56a, and the inclined part 51b for guiding the insertion and the inclined part 51c for guiding the drawing of the pointed part 51a contact the upper inner perimeter of the engaging hole 56a.

In this construction, by inserting the insertion 53 into the connector insertion hole, the pointed part 51a is raised upward, and by inserting further, the pointed part 51a is engaged with the engaging opening 53a similarly to the above mentioned.

At this time, the lower portion of the pointed part 51a is also engaged with the engaging hole 56a of the receiving terminal 56 so as to contact and connect electrically with the receiving terminal 56, whereby the switch is turned on. Even if shavings are generated by the slide of the lower end of the pointed part 51a and the insertion 53 and adhere to the pointed part 51a or are accumulated on the receiving terminal 56, the inclined parts 51b and 51c, which are the side surface of the pointed part 51a, contact and are rubbed with the upper inner perimeter of the engaging hole 56a, whereby the adhering foreign matters are removed and fall down through the engaging hole 56a. Accordingly, when the switch is turned on, the electrical contact part of the rocking terminal 51 and the receiving terminal 56 is always kept in the electrical contact state.

Figure 7:
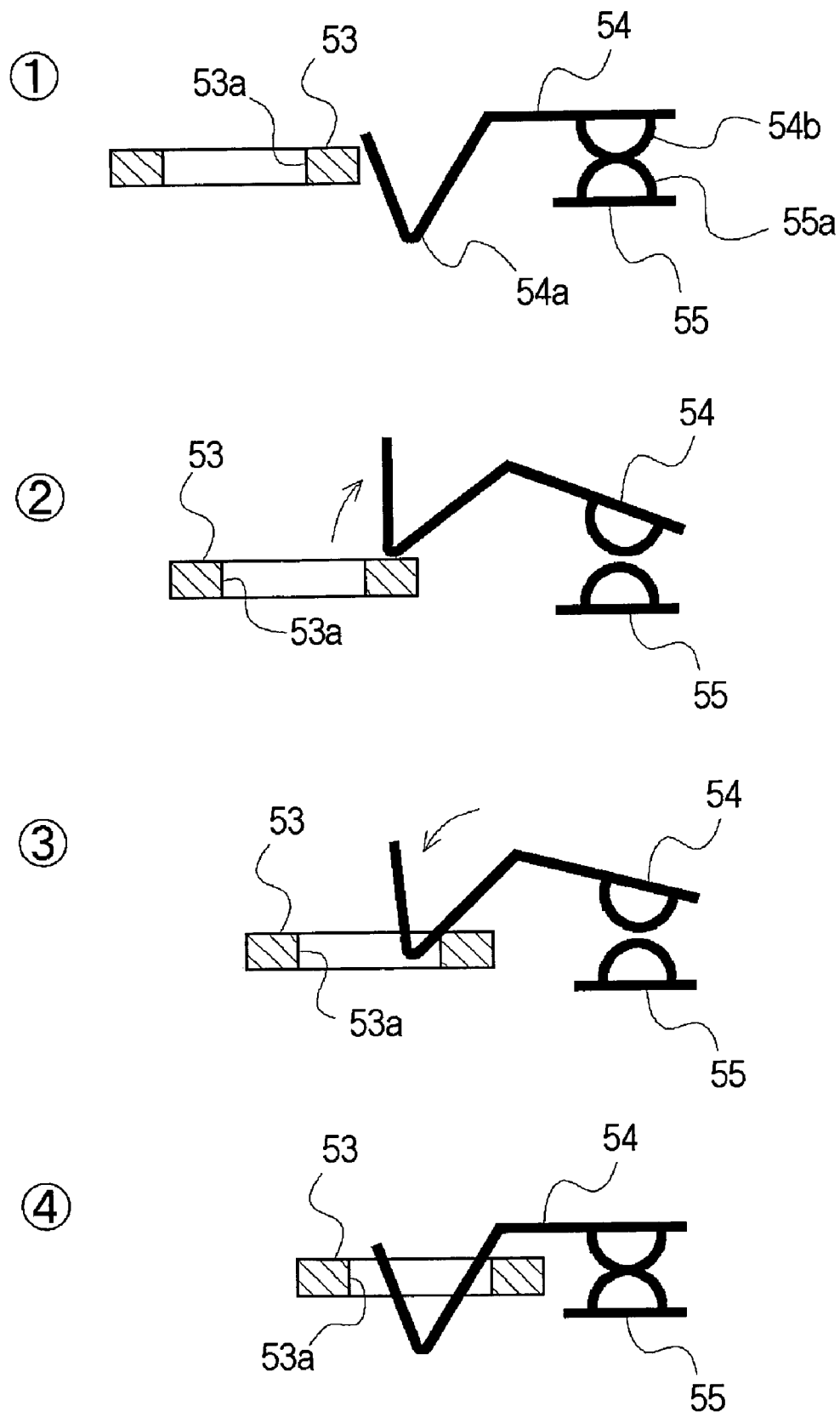
FIG. 7 is a drawing of an embodiment that an pointed part of a rocking terminal is disposed to be separated from an electrical connection part.

Next, explanation will be given on the third embodiment according to FIG. 7.

The switch part comprises a rocking terminal 54 and a receiving terminal 55. The rocking terminal 54 is constructed by electrically-conductive and elastic material, such as spring steel. The basal end of the rocking terminal 54 is fixed to the main body of the connector and connected to the controller (or electrical apparatus). An pointed part 54a is formed at the tip of the rocking terminal 54 similarly to the rocking terminal 51, and a salient 54b is provided projectively downward at the side of the basal end separated from the pointed part 54a, on the lower surface (the surface opposite to the receiving terminal 55) at the position not interfering with the insertion 53.

The basal end of the receiving terminal 55 is fixed to the main body of the connector and connected to the controller (or electrical apparatus). The tip of the receiving terminal 55 is extended to the middle portion of the rocking terminal 54, that is, under the salient 54b separated from the pointed part 54a so that a salient 55a projecting upward is provided on the tip. The salient 55a and 54b are constructed by electrically-conductive members, and contact with each other normally. However, either of the salient 55a and 54b may be omitted. Instead of providing the salient 55a and 54b, the contact parts may be constructed by bending the terminals.

Accordingly, by inserting the insertion 53 into the switch part through the insertion hole of the connecter, the tip of the insertion 53 touches and raises the pointed part 54a, and the pointed part 54a slides on the upper surface of the insertion 53 is inserted into the engaging opening 53a. At this time, the rocking terminal 54 contacts the receiving terminal 55. The salient 54b and 55a contacting electrically by this contact of terminals is separated from the pointed part 54a, that is, the contact part of the rocking terminal 54 and the insertion 53 and the electrical contact part of the rocking terminal 54 and the receiving terminal 55 are arranged separately, whereby the electrical contact parts are not influenced by shavings generated by the contact of the pointed part 54a and the insertion 53 or foreign matters, and the rocking terminal 54 and the receiving terminal 55 contact electrically with each other certainly. In addition, at the place in which the engaging opening 53a is not provided on the insertion 53, the switch part is turned off.

Figure 8:
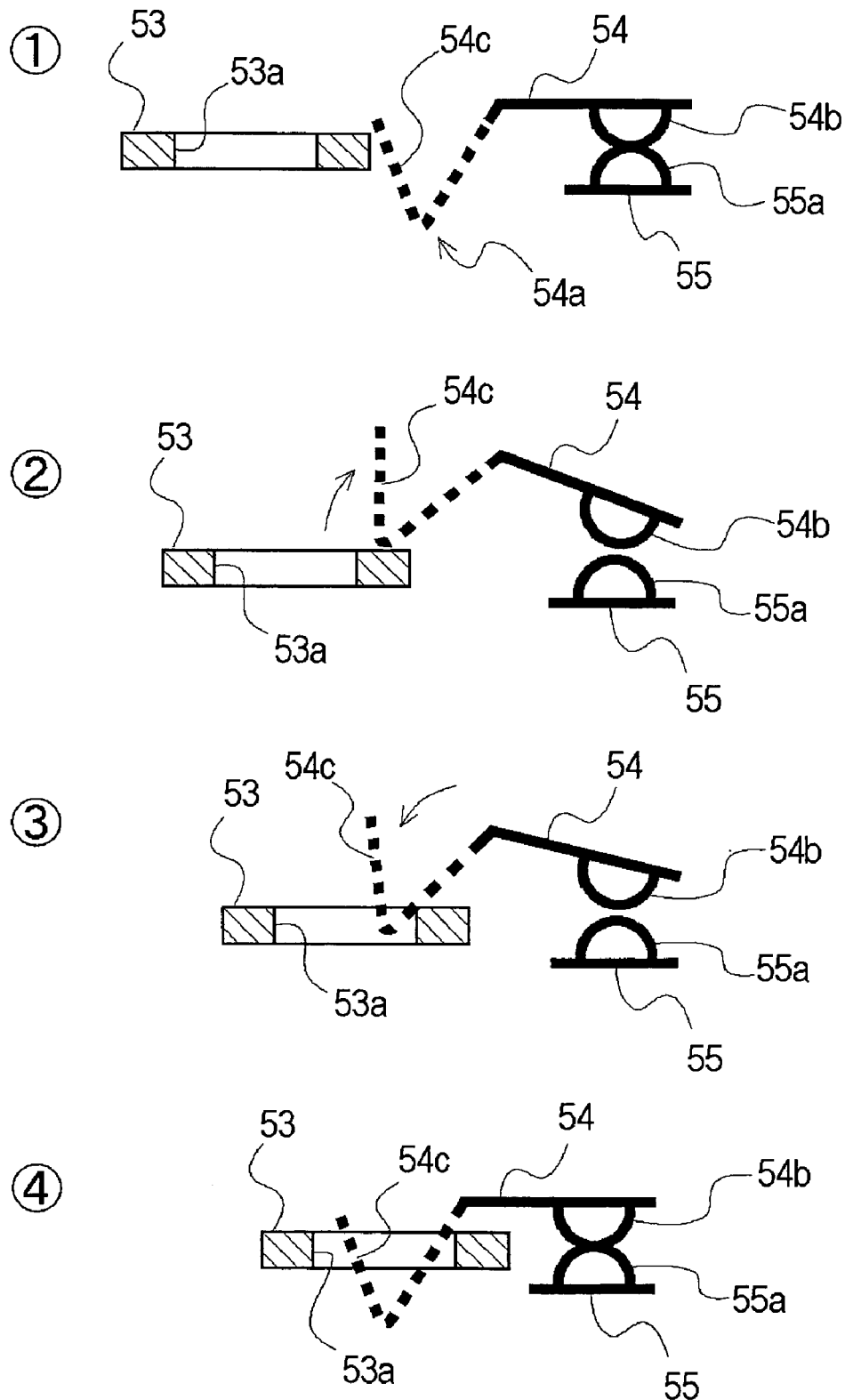
FIG. 8 is a drawing of an embodiment that the pointed part is constructed by a nonconductor.

Next, explanation will be given on the fourth embodiment according to FIG. 8.

The shape of the switch part in the fourth embodiment is substantially the same as that of the third embodiment, and what differs is that the pointed part 54a is constructed by a nonconductor in the fourth embodiment.

Namely, a nonconductive pointed part 54c is formed integrally on the tip of the rocking terminal 54, and the salient 54b is formed at the middle of the lower surface of the rocking terminal 54. Oppositely to the salient 54b, the salient 55a is constructed on the upper surface of the receiving terminal 55. Instead of the nonconductive pointed part 54c constructed integrally by a nonconductor, the part of the pointed part 54a contacting the insertion 53 may be stuck thereon with or coated with a nonconductive member.

Accordingly, the pointed part is constructed as the nonconductive pointed part 54c. Therefore, even if the insertion 53 charged with static electricity is inserted into the connector, the electricity does not flow into the nonconductive pointed part 54c contacting the insertion 53, whereby high voltage is not applied on the controller or the like connected to the rocking terminal 54 so as to prevent the controller or another electrical apparatus to be damaged. In addition, generation of static electricity can be prevented by constructing the insertion 53 by an electric conductor. However, the insertion 53 is constructed by synthetic resin or the like so as to reduce the cost, whereby static electricity tends to be generated.

Figure 9:
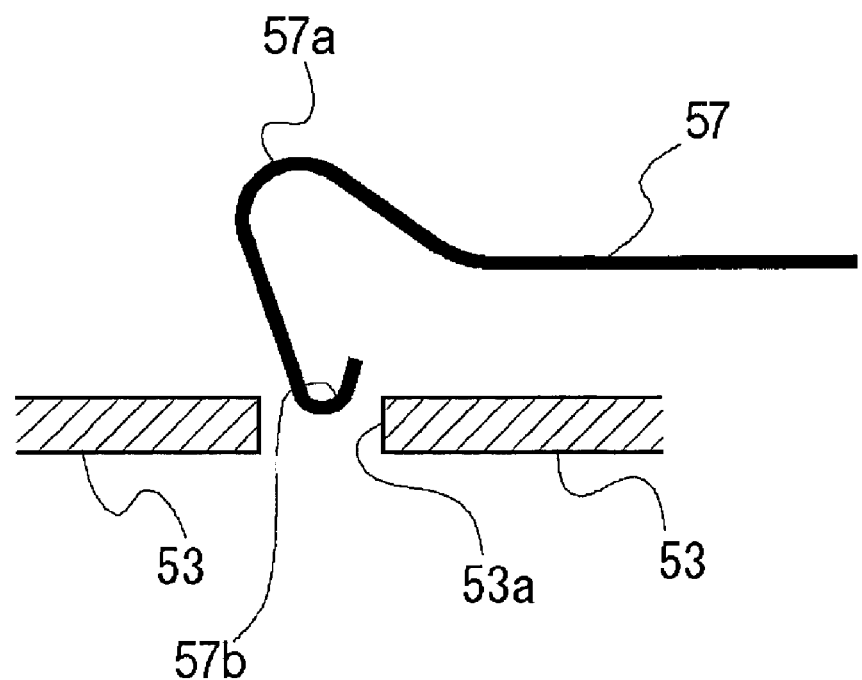
FIG. 9 is a drawing of another embodiment of the pointed part.
Figure 10:
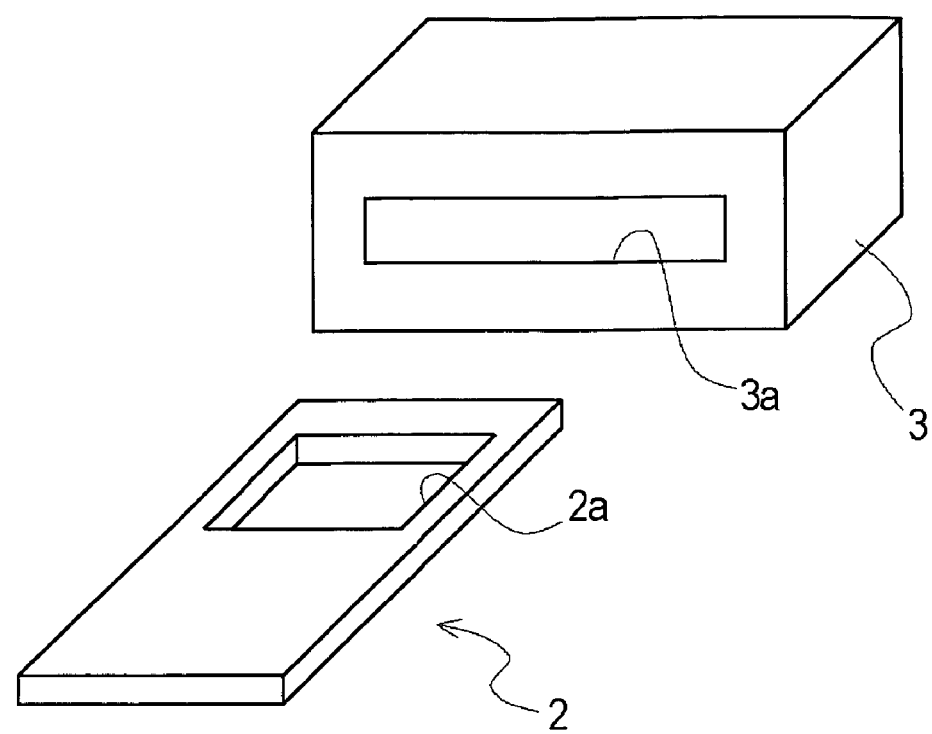
FIG. 10 is a perspective view of the conventional connector 3 and an insertion 2 inserted into the connector 3.
Figure 11:
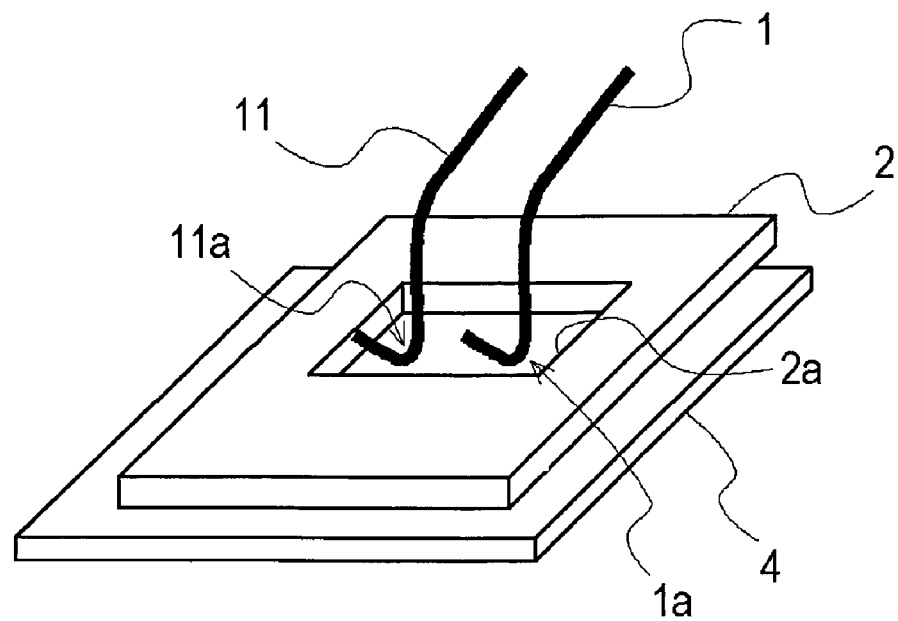
FIG. 11 is a drawing of the pile of the conventional insertion 2, rocking terminals 1 and 11, and terminal plate 4 which the rocking terminal 1 contacts.
Figure 12:
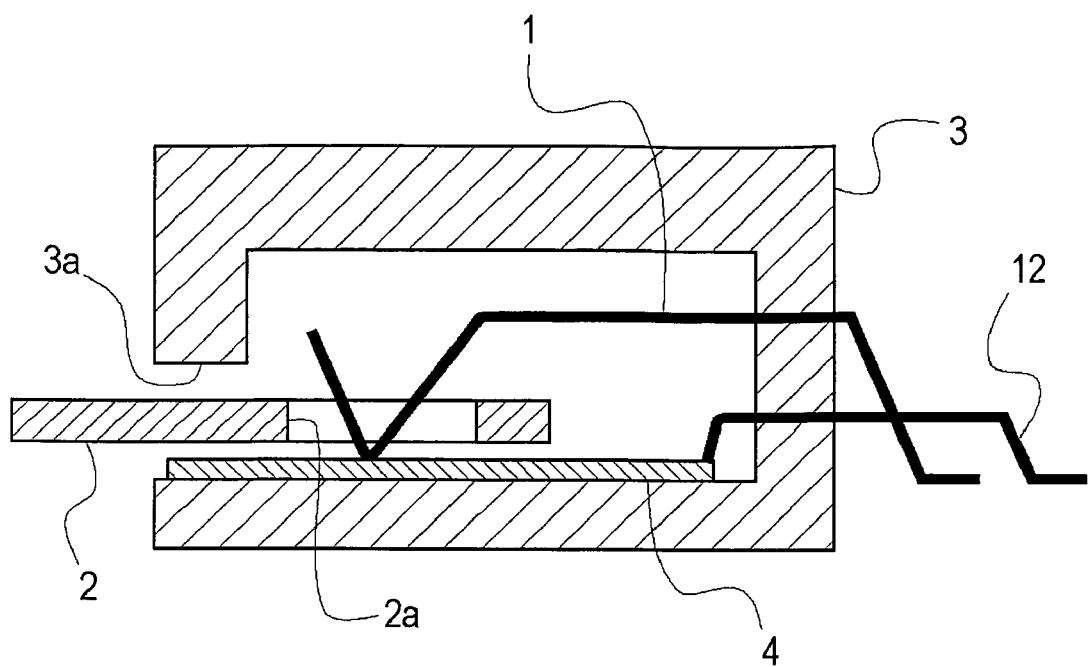
FIG. 12 is a cross-sectional side view of the positional relation among the conventional connector 3, the rocking terminal 1 and a terminal engaging opening 2a opened in the insertion 2.
Figure 13:
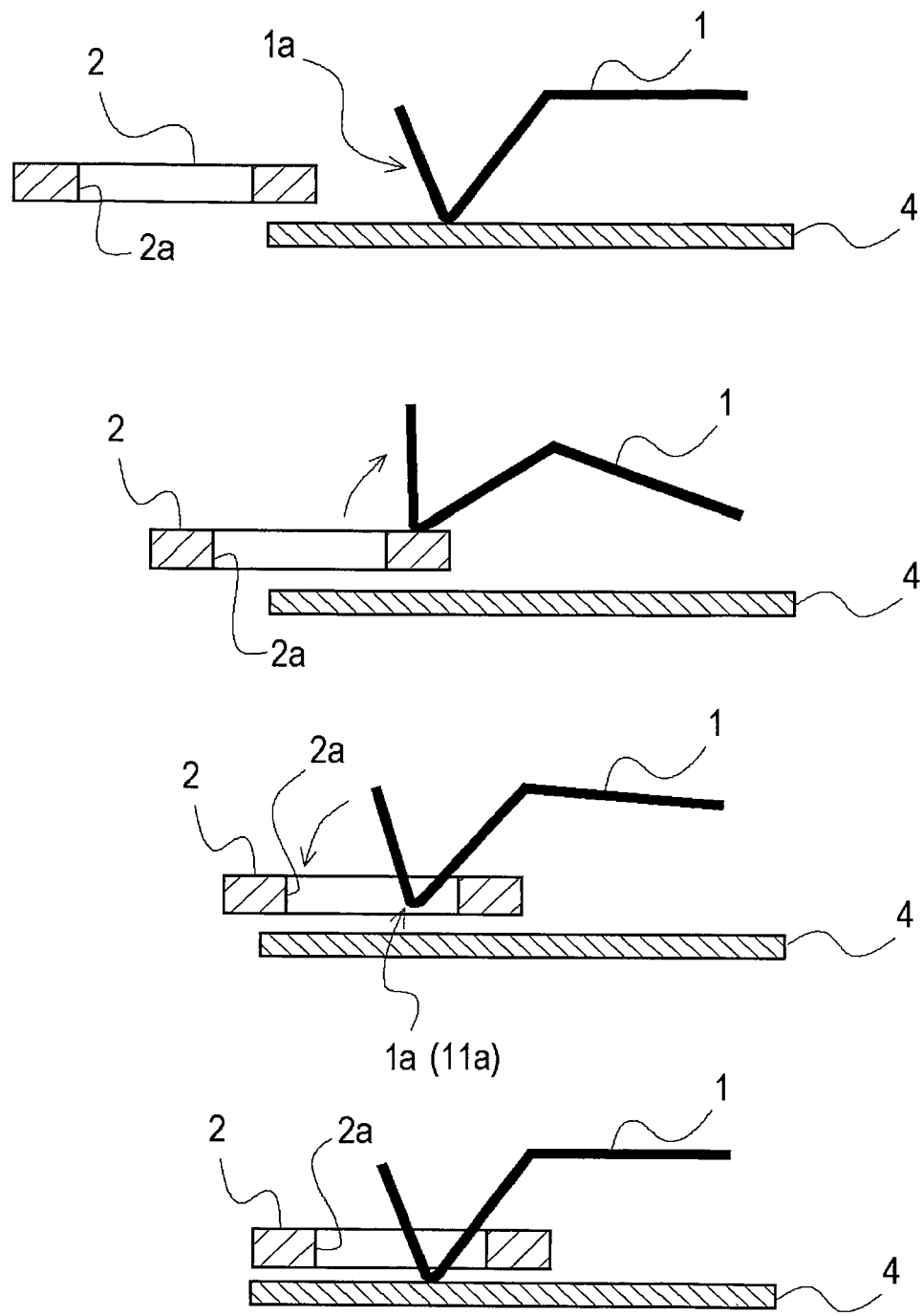
FIG. 13 is a drawing of the insertion 2 inserted into the connector 3 in the conventional construction.

The pointed parts 51a and 54a are not limited to be V-like shaped. As shown in FIG. 9, it may alternatively be constructed so that a rocking terminal 57 is substantially inverted V-like shaped and comprises an upper curved part 57a and a lower curved part 57b.

Namely, what is necessary is just to taper the rocking terminal 57 to the lower portion of the pointed part thereof, that is, the part inserted into the engaging opening 53a so as to form an inclined part which slides smoothly without being caught by anything and raises the rocking terminal 57 at the time of inserting or removing the insertion 53, and to enable the lower end of the rocking terminal 57 to penetrate the engaging opening 53a and contact the receiving terminal at the time of turning on the switch part.

In addition, the positional relation between the rocking terminal 57 and the receiving terminal may be inversed.

Explanation will be given on another embodiment of the present invention according to FIG. 14.

Figure 5:
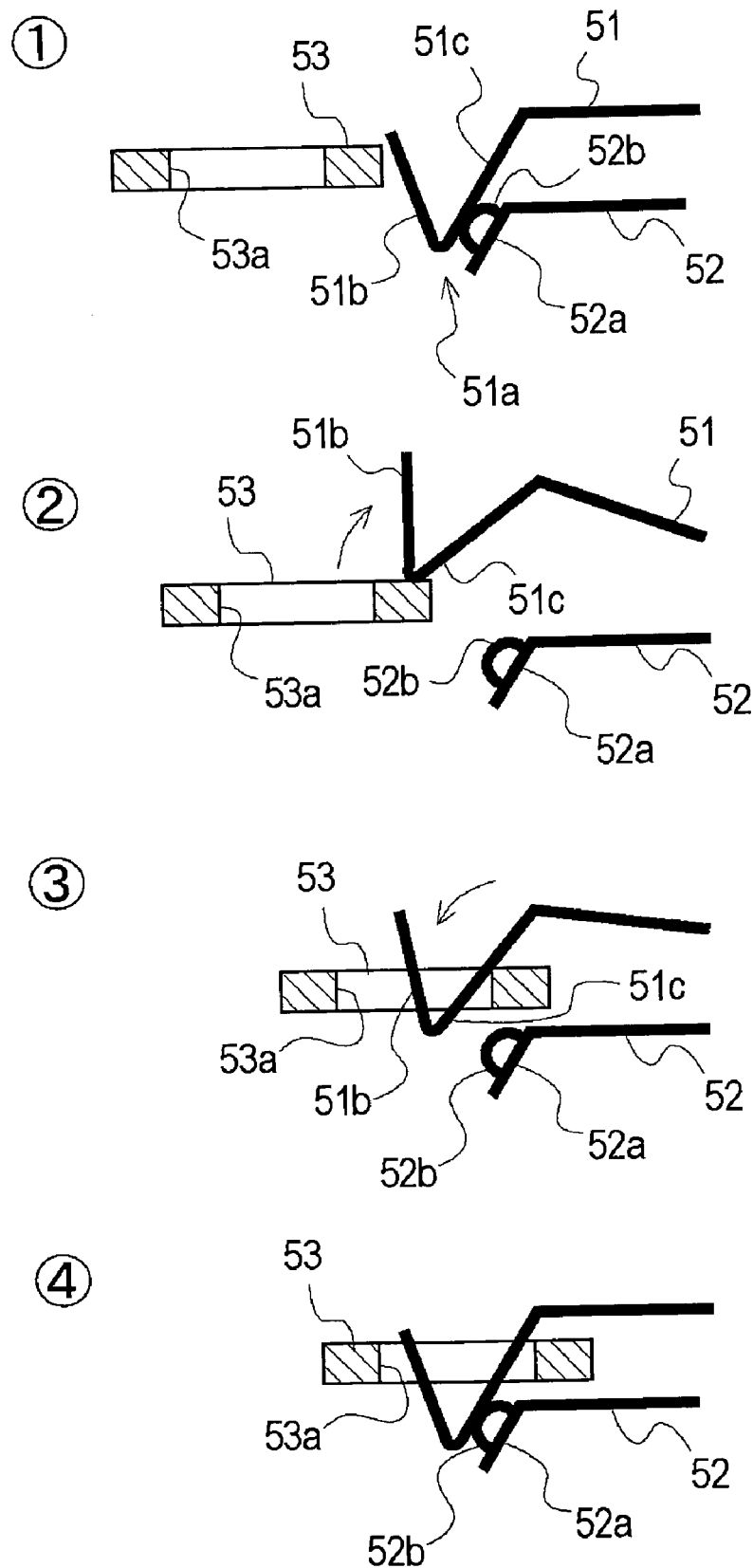
FIG. 5 is a drawing of an embodiment of the switch construction of the present invention.
Figure 14:
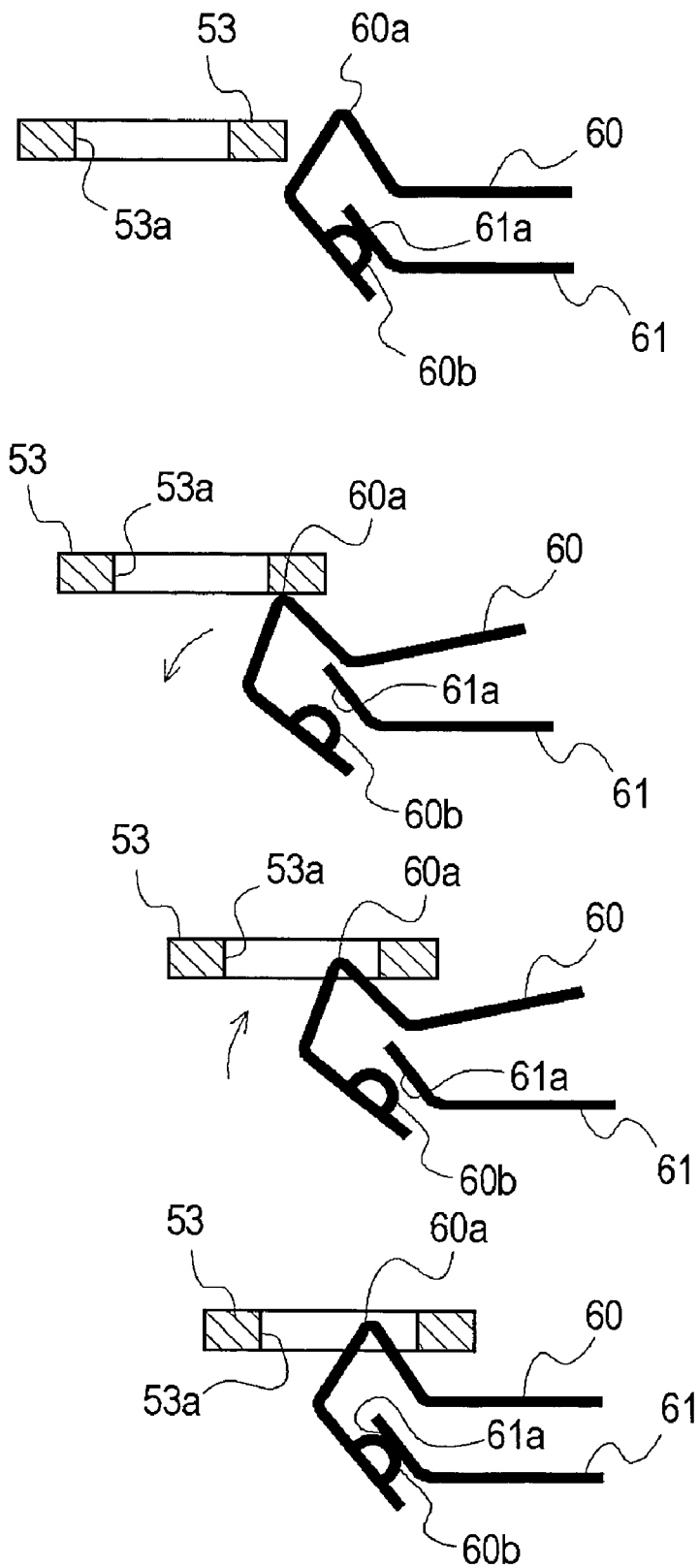
FIG. 14 is a drawing of another embodiment in which the switch construction of the present invention is adopted.

In the embodiment shown in FIG. 14, the shape of rocking terminal 60 and receiving terminal 61 is different from the embodiment shown in FIG. 5.

In the embodiment shown in FIG. 5, the rocking terminal 51 is moved upward against the inserted insertion 53. Contrarily, in the embodiment shown in FIG. 14, the rocking terminal 60 is moved downward against the inserted insertion 53.

In the embodiment shown in FIG. 5, substantially V-shaped pointed part 51a is constructed downward from the rocking terminal 51 so that the pointed part 51a contact and slide on the upper surface of the inserted insertion 53.

Contrarily, in the embodiment shown in FIG. 14, substantially inverted V-like shaped pointed part 60a is constructed upward from the rocking terminal 60 so that the pointed part 60a contact and slide on the lower surface of the inserted insertion 53.

Furthermore, a doglegged part is constructed downward from the pointed part 60a, and a projection is formed on the surface of the doglegged part opposite to the receiving terminal 61 so as to construct a salient 60b which is an electrical contact part. The salient 60b which is the electrical contact part contacts the electrical contact part of an upper bending part 61a at the tip of the receiving terminal 61 so as to contact electrically.

Namely, the salient 60b which is the electrical contact part is constructed upward on the rocking terminal 60 and contacts the upper bending part 61a electrically so that the receiving terminal 61 and the rocking terminal 60 are constructed as a closed circuit characteristically.

In FIG. 14, at the first stage before inserting the inserted insertion 53, the salient 60b which is the electrical contact part of the rocking terminal 60 contacts the upper bending part 61a of the receiving terminal 61 by the elastic force of the rocking terminal 60 and the receiving terminal 61.

At the second stage, the inserted insertion 53 is inserted and touches the pointed part 60a of the rocking terminal 60 so as to push the rocking terminal 60 down, whereby the contact of the salient 60b which is the electrical contact part and the upper bending part 61a is canceled.

At the third stage, the inserted insertion 53 is pushed further and the pointed part 60a reaches the engaging opening 53a of the insertion 53, whereby the rocking terminal 60 starts to be moved upward by the elastic force.

At the fourth stage, the pointed part 60a of the rocking terminal 60 rises in the engaging opening 53a so that the salient 60b which is the electrical contact part and the upper bending part 61a contact with each other again.

INDUSTRIAL APPLICABILITY

The present invention can be used at the use application at which no contact tends to occur by shavings generated by inserting an insertion or foreign matters because of high frequency of the inserting of the insertion into a connector or the air pollution around the connector, such as a process controller at the scene of labor of the manufacturing or various systems in the open air.

The invention claimed is:

1. A connector having a switch part comprising a rocking terminal swayed by inserting an insertion into a main body of the connector and a receiving terminal arranged to contact the rocking terminal, characterized in that
the rocking terminal engages with an opening in the insertion when the insertion is inserted into the main body of the connector;
a pointed part is formed on the rocking terminal; and
the terminals contact electrically with each other by making the receiving terminal touch an outside surface of an inclined part of the pointed part.

2. The connector as set forth in claim 1, wherein
the receiving terminal is provided at a position opposite to the rocking terminal,
the pointed part of the rocking terminal is pointed,
an engaging part is provided on the receiving terminal at a position opposite to the pointed part, and
the terminals contact electrically with each other by making the engaging part and the pointed part engage with each other.

3. A connector having a switch part comprising a rocking terminal swayed by inserting an insertion into a main body of the connector and a receiving terminal arranged to contact the rocking terminal, characterized in that
the rocking terminal engages with an opening in the insertion when the insertion is inserted into the main body of the connector;
the rocking terminal has a basal end fixed to the main body of the connector and a tip to be inserted through the insertion;
a part of the rocking terminal slidingly contacting the insertion inserted into the connector and a part of the rocking terminal electrically contacting the receiving terminal are constructed separately; and
a salient provided adjacent the basal end of the rocking terminal and/or on the receiving terminal.

4. The connector as set forth in claim 3, wherein
a pointed part is formed on the rocking terminal, and
an electrical contact part of the rocking terminal and the receiving terminal is constructed to be separated from the pointed part.

5. The connector as set forth in claim 3, wherein
a pointed part is formed on the rocking terminal, and
an electrical contact part contacting the receiving terminal is constructed on a doglegged part of the rocking terminal at a position near and above or below the pointed part.

6. The connector as set forth in claim 3, wherein
the part of the rocking terminal slidingly contacting the insertion is constructed by a nonconductor.

* * * * *